United States Patent [19]

Lebacq

[11] Patent Number: 5,407,552
[45] Date of Patent: Apr. 18, 1995

[54] ELECTROPHORESIS DEVICE

[75] Inventor: Philippe Lebacq, Paris, France

[73] Assignee: Bioprobe Systems, Paris, France

[21] Appl. No.: 150,195

[22] PCT Filed: Jun. 3, 1992

[86] PCT No.: PCT/FR92/00491

§ 371 Date: Dec. 9, 1993

§ 102(e) Date: Dec. 9, 1993

[87] PCT Pub. No.: WO93/00583

PCT Pub. Date: Jan. 7, 1993

[30] Foreign Application Priority Data

Jun. 20, 1991 [FR] France .................. 91 07586

[51] Int. Cl.6 ............................................. B01D 61/42
[52] U.S. Cl. ............................................. 204/299 R
[58] Field of Search .................. 204/299 R, 182.8

[56] References Cited

U.S. PATENT DOCUMENTS 3,932,265  1/1976  Hoefer .............................. 204/299 R
3,980,540  9/1976  Hoefer .............................. 204/299 R
4,035,377  7/1977  Detroy .............................. 204/299 R
4,142,960  3/1979  Hahn et al. ....................... 204/180 G
4,339,327  7/1982  Tyler ................................. 204/180 G
4,715,942 12/1987  Tezuka et al. .................... 204/299 R
4,915,811  4/1990  Yamamoto et al. ............... 204/299 R

FOREIGN PATENT DOCUMENTS 1021287  3/1966  United Kingdom .
8600708  1/1986  WIPO .

*Primary Examiner*—John Niebling
*Assistant Examiner*—Edna Wong
*Attorney, Agent, or Firm*—Dennison, Meserole, Pollack & Scheiner

[57] ABSTRACT

An electrophoresis device having a single-piece cartridge (10) filled with a suitable and optionally dyed gel (26) and made from a section of a hollow shape having two opposite open sides (20,22), one of which is sealed by a removable comb element (28) for forming imprints in the gel (26), while the other is sealed by a removable cover (36).

20 Claims, 2 Drawing Sheets

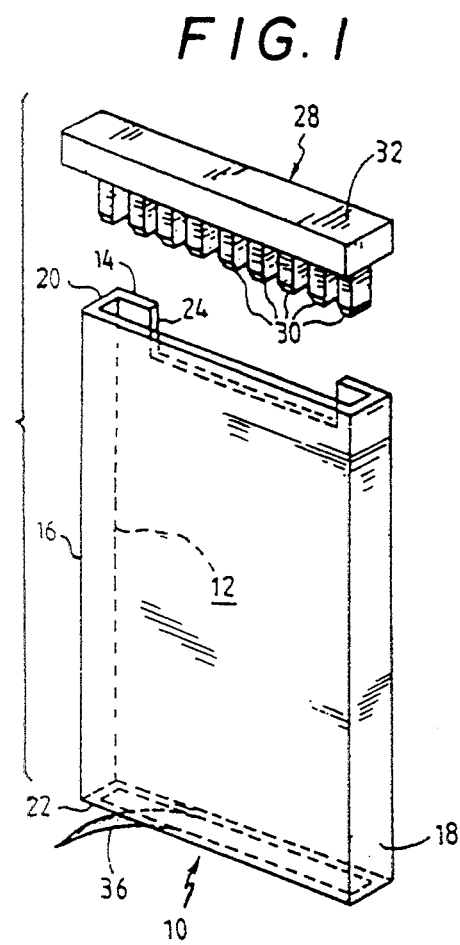
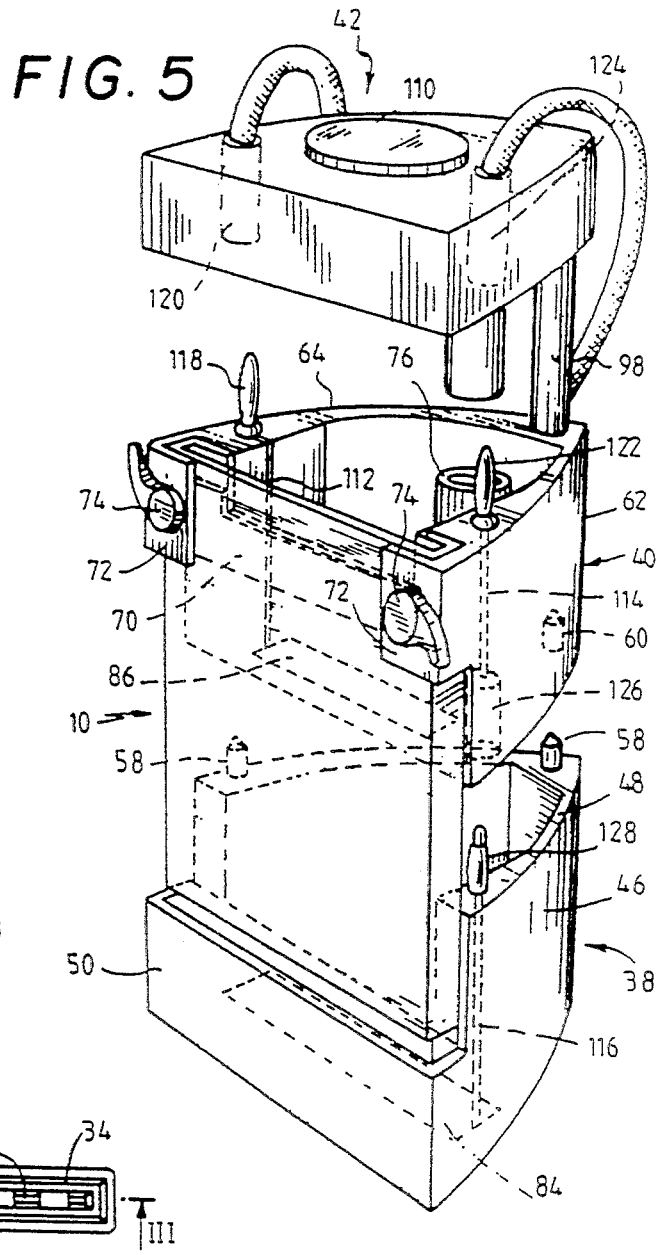
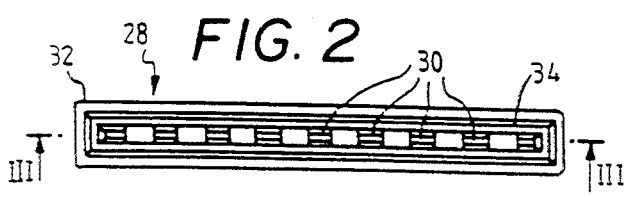
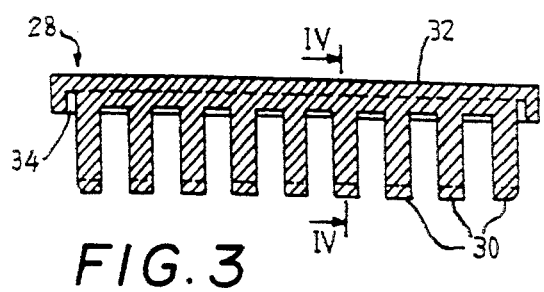
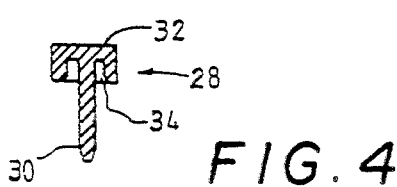

ELECTROPHORESIS DEVICE

BACKGROUND OF THE INVENTION

Field of the Invention

The invention relates to an electrophoresis device.

Electrophoresis is a technique used for the analysis and separation of molecules of different sizes and chemical natures such as nucleic acids, amino-acids, proteins, etc.

The technique is based on the fact that, under the effect of an electric field, molecules of this type migrate within a substrate medium at different speeds according to their charge density and their size.

Electrophoresis is generally carried out on a solid substrate such as a gel, for example, a polyacrylamide or agarose gel, within which the molecules to be analysed or separated migrate at different speeds.

After a given migration period, during which the molecules are subject to the effect of an electric field, they are displaced within the substrate by a given distance which is proportional to their speed of migration and which is therefore correlated to their charge density and their size.

With the use of a suitable dye, the regions reached by the different types of molecules at the end of a given period can be displayed in the form of bands.

Up to the present time, truly automated electrophoresis has not been possible, in particular, because of the difficulty of preparing the substrates necessary for the application of this method.

Polyacrylamide gels which are pre-poured onto a support plate of plastics material are already known. However, these substrates are only suitable for so-called "horizontal" electrophoresis, in which the plates are disposed horizontally.

For so-called "vertical" electrophoresis, in which the support plates are disposed vertically, two glass plates and two glass inserts, which are greased and then assembled and held together by suitable means such as an adhesive tape, are generally used.

A comb is then placed at one end of the support produced and a gel is poured into the space between the two glass plates.

The manufacture of the support plates requires a large number of operations which is not compatible with the automation of the electrophoresis technique.

SUMMARY OF THE INVENTION

The object of the invention is, in particular, to overcome the problems mentioned above.

A particular object of the invention is to obtain an electrophoresis device which provides all the means necessary for the automated implementation of an electrophoresis technique.

According to an essential characteristic of the invention, the electrophoresis device comprises a one-piece cassette filled with a suitable gels which may possibly be dyed, the cassette being produced from a length of hollow profiled section having two opposed open faces, of which one is blocked by a removable comb which can form impressions in the gel, and the other by a detachable cover.

The support thus obtained can be produced on a large scale, and therefore cheaply, and can be delivered to the user ready for use.

The cassette is advantageously in the general form of a right-angled parallelepiped defined by two large, parallel and opposed faces disposed close to each other and joined together by two small, parallel and opposed faces.

According to another characteristic of the invention, the cassette comprises a lateral cut-out portion opening into the open face which receives the removable comb, the lateral cut-out portion also being blocked by the comb when the latter is placed on the aforementioned open face.

When the comb has been removed from the cassette, the lateral cut-out portion thereof is thus uncovered to allow electrical contact with the gel at the corresponding end of the cassette, as will be seen below.

Another electrical contact can be made at the other end of the cassette, after the detachable cover has been removed.

The cover is advantageously ultrasound-welded to the corresponding open face of the cassette.

The cassette is advantageously produced from an extruded profile of a plastics material which is transparent to ultraviolet rays.

According to another characteristic of the invention, the device also comprises two tanks, each suitable for containing a conductive buffer, and containing two respective electrodes which can be supplied by a direct-current supply, the two tanks having respective openings for the two open faces of the cassette, to ensure contact between the gel and the corresponding buffer of each tank.

Although the invention can equally well be applied to horizontal electrophoresis and to vertical electrophoresis, it is preferably applied to vertical electrophoresis.

In this case, the device comprises a lower tank and an upper tank which are superposed vertically in order to house the cassette in a vertical positions one end of the cassette being immersed in the lower tank and the other end of the cassette communicating with the upper tank laterally.

The upper tank advantageously comprises a vertical wall in which a lateral opening is formed to ensure that the buffer is put in contact with the gel of the cassette through a lateral cut-out portion in the cassette, a sealing gasket being provided on the said vertical walls near its lateral opening.

According to another characteristic of the invention, the lower tank and the upper tank are separable and a separable lid, which can be fitted on the upper tank, is also provided.

This characteristic has the particular advantage that it facilitates the cleaning of the device.

Advantageously, the upper tank comprises two electrical connections with contacts which can ensure the electrical supply of the two electrodes when the lid is fitted on the upper tank and, at the same time, the latter is fitted on the lower tank.

This characteristic is particularly advantageous for the safety of the user, on account of the high electrical voltages applied to the electrodes.

To advantage, the base wall of the upper tank comprises an overflow duct enabling the lower tank to be filled when the buffer in the upper tank overflows into the duct.

The device preferably also comprises clamping means for holding the cassette in a vertical position, the clamping means being provided, for example, on the upper tank.

The device advantageously also comprises a programmer interposed between the electrodes and the voltage supply for adjusting the electrophoresis period as desired.

The device also advantageously comprises a concentrated dose of buffer which, after dilution, enables the two tanks to be filled to the desired level.

BRIEF DESCRIPTION OF THE DRAWINGS

In the following description, which is given solely by way of example, reference will be made to the appended drawings, in which:

FIG. 1 is an exploded, perspective view of a cassette forming part of the device of the invention;

FIG. 2 is a view of the comb of the cassette of FIG. 1, from below;

FIG. 3 is a section taken on the line III—III of FIG. 2:

FIG. 4 is a section taken on the line IV—IV of FIG. 3;

FIG. 5 is an exploded, perspective view of the device of the invention, the lower tank, the upper tank, and the lid being separated;

DESCRIPTION OF THE INVENTION

Figure 6:
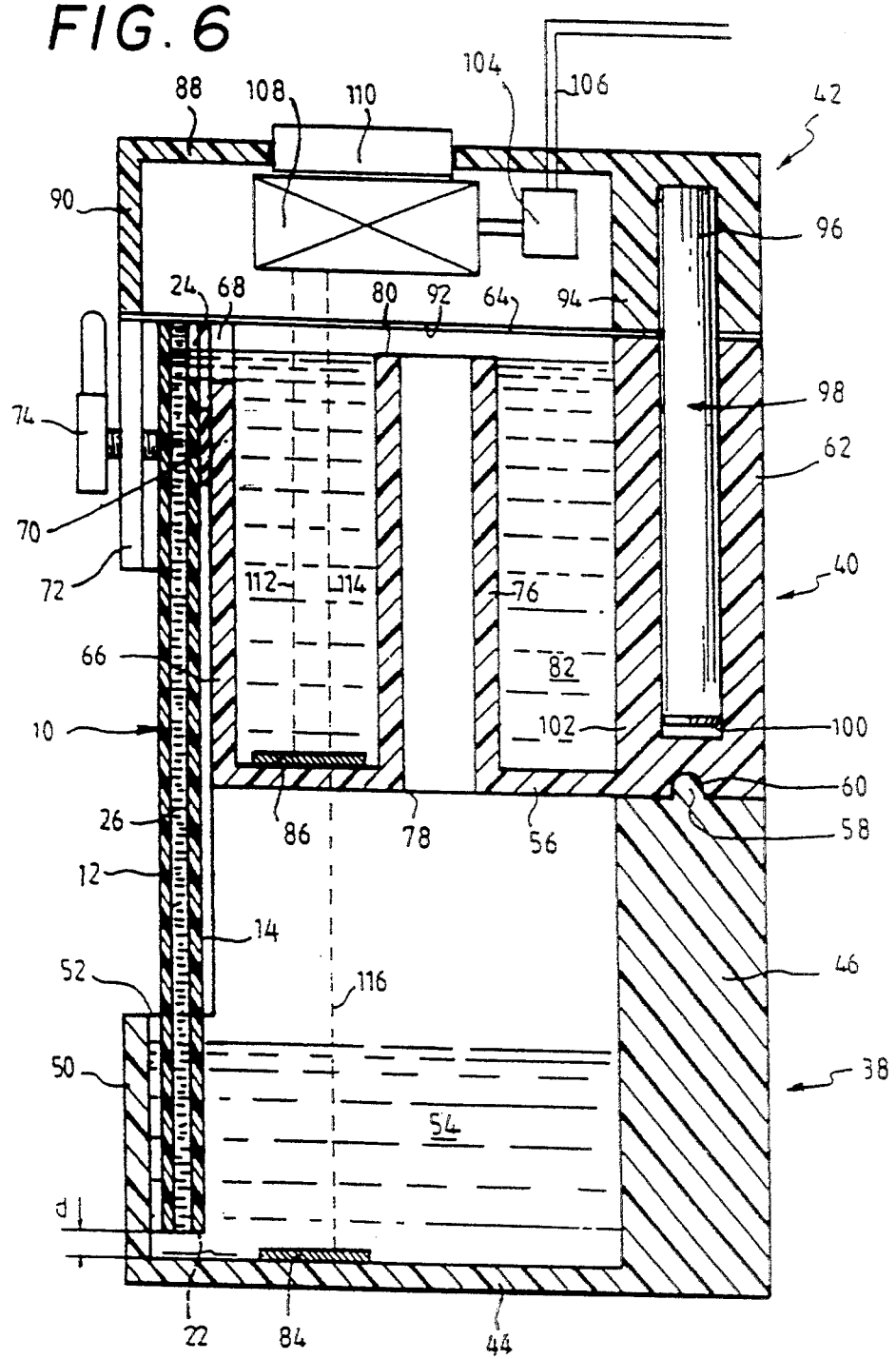
FIG. 6 is a vertical section of the device of FIG. 5, the lower tank, the upper tank and the lid being joined together.

Reference will first be made to FIG. 1 which shows a cassette 10 formed by a single piece of an extruded profiled section of a plastics material which is transparent to ultraviolet rays.

The cassette 10 is in the general form of right-angled parallelepiped defined by two large, parallel and opposed faces 12 and 14 disposed close to each other and joined together by two small, parallel and opposed faces 16 and 18. The cassette 10 has two opposed open faces: an upper open face 20 and a lower open face 22, both with generally rectangular outlines.

Beside the open face 20, the face 14 of the cassette 10 has a generally rectangular lateral cut-out portion 24 which extends almost throughout the width of the cassette and opens into the open face 20.

By way of example, the cassette 10 may be about 100 mm high and about 70 mm wide and may have an internal space of about 2 mm between the facing faces 12 and 14. The lateral cut-out portion 24 may be about 60 mm wide and generally less than 10 mm high.

The cassette 10 is intended to contain a gel 26 (FIG. 6) such as a polyacrylamide gel or an agarose gel, for example. The gel may be dyed by means of a suitable dye, for example, ethidium bromide.

The open face 20 can be blocked by a comb 28 having a plurality of teeth 30 suitable for forming impressions (not shown) in the gel 26 when the comb 28 is placed on the open face 20.

The comb 28 (FIGS. 2 to 4) comprises an elongate right-angled parallelepipedal base 32 from which the teeth extend. The base 32 has a peripheral groove 34 of a shape matching that of the outline of the open face 20 of the cassette. When the comb 28 is put in place on the open face 20, it blocks the lateral cut-out portion 24 at the same time.

The open face 22 is blocked by a detachable cover 36 constituted, for example, by a thin sheet of aluminium covered with a coating of plastics material which can be ultrasound-welded to the open face 22 of the cassette.

The cassette 10 is produced from an extruded profiled section formed of a plastics material which is transparent to ultraviolet rays. In the factory, the cassette 10 is provided with its comb 28 and is then disposed vertically with its comb at the bottom to enable the gel 26 to be poured up to the level of the open face 22 which is placed in the upper position. The comb 28 thus forms a certain number of impressions in the gel. After the gel has been poured, the cassette is provided with its cover 36 and can thus be sent to the user.

In order to carry out electrophoresis, after having removed the comb 28 and the cover 36 therefrom, the user fits the cassette 10 on a suitable device such as that shown in FIGS. 5 and 6.

This device comprises a lower tank 38 and an upper tank 40 which are superposed vertically in order to house a cassette 10 in a vertical position with the open face 22 oriented downwardly, as well as a lid 42 which can be fitted on the top of the upper tank 40. The tanks 38 and 40 are advantageously formed from a transparent plastics material.

The lower tank 38 is defined by a base wall 44 surmounted by a lateral wall 46 with a generally U-shaped horizontal upper edge 48 and by a front face 50 which is connected to the wall 46. The front face 50 extends to a height lower than that of the lateral wall 46 and forms a generally rectangular horizontal opening 52 which fits the cross-section of the cassette 10.

The lower tank 38 is suitable for containing an electrically-conductive buffer 54, the depth to which it is filled with the buffer being less than the height of the wall 50.

It will be appreciated that the end of the cassette 10 with the open face 22 can be immersed in the buffer 54 so that the buffer comes into contact with the gel 26 at the end with the open face 22. For this purpose, it is essential that the open face be disposed at a distance d (FIG. 6) from the base wall 44.

The upper tank 40 comprises a base wall 56 which can rest on the upper edge 48 of the tank 38 and can be fitted on this edge with the aid of at least one stud 58 which projects from the edge 48 and can be fitted in a corresponding seat 60 in the base wall 56.

The tank 40 is also defined by a lateral wall 62 having a U-shaped upper horizontal edge 64. The tank 40 is also defined by a vertical front wall 66 against which the face 14 of the cassette 10 is applied in a vertical position. For this reason, the front face 12 is not superposed vertically on the front face 50 of the tank 38.

The upper portion of the vertical wall 66 defines a lateral opening 68 which is disposed facing the lateral cut-out portion 24 of the cassette 10 (FIG. 6).

The front wall 66 has a sealing gasket 70 for ensuring a leakproof joint with the face 14 of the cassette 10 around and below the lateral opening 68.

The tank 40 also comprises two lugs 72 which are turned inwardly and connected to the wall 62 and each of which has a clamping member 74 which can press the upper portion of the cassette 10 towards the wall 66 and, as a result, compress the sealing gasket 70.

The clamping members 74 also hold the cassette in a position such that its lower open face 22 is disposed at a distance from the base 44. If necessary, wedges (not shown) could be provided on the base wall 44 to allow for the distance d.

The tank 40 also comprises an overflow duct 76 of which the lower end 78 is connected to the base wall 56 and the upper end 80 opens at a distance from the edge 64. This distance, however, is less than the height of the lateral opening 68.

The upper tank 40 is intended to contain a buffer 82 identical to the buffer 54 in the tank 38.

In order to fill the two tanks, a suitable quantity of buffer is poured into the upper tank 40 in a manner such that the buffer level 82 reaches the upper end 80 of the duct 76 and the buffer then overflows into the lower tank 38.

It will be appreciated that the buffer 82 comes into contact with the gel 26 through the lateral opening 68 in the tank 40 and through the lateral cut-out portion 24 in the cassette 10.

The tanks 38 and 40 contain, respectively, an electrode 84 (in the embodiment shown, an anode) and an electrode 86 (in the embodiment shown, a cathode) which can be connected to a suitable voltage supply.

The lid 42 comprises an upper wall 88, from which there extends a side wall 90 with a closed periphery and having a lower edge 92 which can rest on the upper edge 64 of the tank 40.

Fitted in a thickened portion 94 of the wall 90 is the end 96 of a vertical column 98 which can slide and pivot in a cylindrical housing 100 with a vertical axis formed in a thickened portion 102 of the wall 62 of the tank 40.

The lid 42 can thus be moved away from or towards the tank 40, in particular, to allow the tanks 38 and 40 to be filled.

The lid 42 houses a current rectifier 104 which can be connected to the mains by a supply cable 106. The rectifier supplies a direct-current voltage which can be regulated, for examples up to 2000 V, this voltage then being applied to the electrodes 84 and 86 by means of a programmer 108. The latter is controlled by a rotary knob 110 projecting above the lid.

The electrode 86 is supplied by means of an electrical connection 112 which extends throughout the depth of the tank 40 and the electrode 84 is supplied by an electrical connection 114 extending throughout the depth of the tank 40 and an electrical connection 116 extending throughout the depth of the tank 38.

As shown in greater detail in FIG. 5, the connection 112 terminates at the top in a male plug 118 for cooperating with a female socket 120 housed in the lid 42 when the latter is fitted on the tank 40.

The connection 114 terminates at the top in a male plug 122 for cooperating with a female socket 124 housed in the lid. The connection 114 terminates at the bottom in a female socket 126 for cooperating with a male plug 128 which is mounted on the upper end of the connection 116.

When the two tanks 38 and 40 are fitted together and the lid 42 is fitted, electrical connection with the electrodes 84 and 86 is thus ensured.

Figure 7:
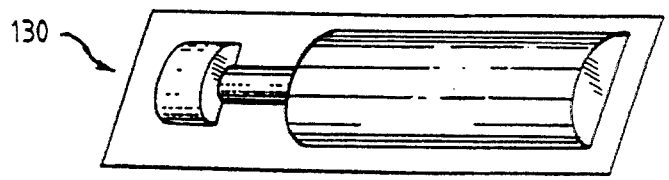
FIG. 7 is a perspective view of a container containing a concentrated dose of buffer.

FIG. 7 shows a container 130, for example, of the "blister" type, containing a concentrated dose of buffer which, after suitable dilution, enables the two tanks to be filled to the desired level.

The device of the invention is used in the following manner: the user first removes the comb 28 and the cover 36 from the cassette 10 and then places the sample(s) to be analysed in the wells formed in the gel 26.

He then puts the cassette in place in a vertical position, holding it firmly with the clamping elements 74, a distance d being allowed between the open face 22 of the cassette and the base AA of the tank 38 (FIG. 6).

A direct-current voltage is then applied between the two electrodes, the voltage value being regulated and the period of operation being adjusted by means of the programmer 108.

The negatively-charged molecules are displaced vertically from the cathode towards the anode, that is, downwardly from the top. At the end of a given electrophoresis period, the regions in which the molecules which have migrated are situated are displayed by coloured bands.

Although the invention has been described with particular reference to a device in which the cassette is in a vertical position, it also applies to electrophoresis in a horizontal position.

Similarly, the invention is not limited to one-dimensional electrophoresis. It could also be applied to two-dimensional electrophoresis, the cassette being turned through 90° between two successive operations. In this case, it would be necessary to provide openings through the two small faces 16 and 18 of the cassette.

The invention may be used for the separation and analysis of molecules of various kinds such as nucleic acids, amino-acids, proteins, etc.

I claim:

1. Electrophoresis device, characterized in that it comprises a one-piece cassette (10) filled with an electrophoresis gel (26), the cassette being produced from a length of a hollow profiled section having two opposed open faces (20, 22), of which one is blocked by a removable comb (28) for forming impressions in the gel (26), and the other by a detachable cover (36).

2. Device according to claim 1, characterized in that the cassette (10) is in the form of a right-angled parallelepiped defined by two large, parallel and opposed faces (12, 14) disposed close to each other and joined together by two small, parallel and opposed faces (16, 18).

3. Device according to claim 1, characterized in that the cassette (10) comprises a lateral cut-out portion (24) opening into the open face (20) which receives the removable comb (28), the lateral cut-out portion being blocked by the comb (28) when the latter is placed on the aforementioned open face.

4. Device according to claim 1, characterized in that the cassette (10) is produced from an extruded profile of a plastics material which is transparent to ultraviolet rays.

5. Device according to claim 1, characterized in that the cover (36) is ultrasound-welded to the corresponding open face (22) of the cassette (10).

6. Device according to claim 1, characterized in that it also comprises two tanks (38, 40), each for containing a conductive buffer, (54, 82) and containing two respective electrodes (84, 86) for connecting a direct-current supply, the two tanks having respective openings (52, 68) for the two open faces of the cassette (10) to ensure contact between the gel (26) and the corresponding buffer (54, 82) of each tank.

7. Device according to claim 6, characterized in that the two tanks comprise a lower tank (38) and an upper tank (40) which are superposed vertically in order to house the cassette (10) in a vertical position, one end of the cassette being immersed in the lower tank (28) and the other end of the cassette communicating with the upper tank (40) laterally.

8. Device according to claim 7, characterized in that the upper tank (40) comprises a vertical wall (66) in which a lateral opening (68) is formed to ensure that a buffer (82) is put in contact with the gel (26) of the cassette through a lateral cut-out portion (24) of the cassette, a sealing gasket (70) being provided on the vertical wall (66) near its lateral opening (68).

9. Device according to claim 7, characterized in that the lower tank (38) and the upper tank (40) are separable and in that a separable lid (42), for fitting on the upper tank (40), is also provided.

10. Device according to claim 9, characterized in that the upper tank (40) comprises two electrical connections (112, 114) with contacts ensuring the electrical supply of the two electrodes (84, 86) when the lid (42) is fitted on the upper tank (40) and, at the same time, the latter is fitted on the lower tank (38).

11. Device according to claim 7, characterized in that the upper tank (40) comprises a base wall (56) from which an overflow duct (76) extends to enable the lower tank (38) to be filled when the buffer in the upper tank overflows into the overflow duct.

12. Device according to claim 7, characterized in that it comprises clamping means (74) for holding the cassette (10) in a vertical position.

13. Device according to claim 7, characterized in that it comprises a programmer (108) interposed between the electrodes (84, 86) and the voltage supply for adjusting the electrophoresis period as desired.

14. Electrophoresis device, characterized in that it comprises a one-piece cassette (10), the cassette being produced from a length of a hollow profiled section having two opposed open faces (20, 22), of which one is blocked by a removable comb (28), and the other by a detachable cover (36).

15. Device according to claim 14, characterized in that the cassette (10) is in the form of a right-angled paralellepiped defined by two large, parallel and opposed faces (12, 14) disposed close to each other and joined together by two small, parallel and opposed faces (16, 18).

16. Device according to claim 14, characterized in that the cassette (10) comprises a lateral cut-out portion (24) opening into the open face (20) which receives the removable comb (28), the lateral cut-out portion being blocked by the comb (28) when the latter is placed on the aforementioned open face.

17. Device according to claim 14, characterized in that the cassette (10) is produced from an extruded profile of a plastics material which is transparent to ultraviolet rays.

18. Device according to claim 14, characterized in that the cover (36) is ultrasound-welded to the corresponding open face (22) of the cassette (10).

19. A kit for electrophoretic analysis comprising:
a one-piece cassette (10) filled with a gel (26), the cassette being produced from a length of a hollow profiled section having two opposed open faces (20, 22), of which one is blocked by a removable comb (28) which can form impressions in the gel (26), and the other by a detachable cover (36);
two tanks (38, 40), each said tank containing a conductive buffer, (54, 82) and containing two respective electrodes (84, 86) for connecting a direct-current supply, the two tanks having respective openings (52, 68) for the two open faces of the cassette (10) to ensure contact between the gel (26) and the corresponding buffer (54, 82) of each tank; and
a container (130) containing a concentrated dose of buffer which, after dilution, enables the two tanks (38, 40) to be filled.

20. Device according to claim 15, characterized in that at least one corner of said right-angled parallelepiped cassette is round.

* * * * *